United States Patent [19]

Calton et al.

[11] 4,166,764

[45] Sep. 4, 1979

[54] PRODUCTION OF MONORDEN

[75] Inventors: Gary J. Calton, Elkridge; Marlin A. Espenshade, Ellicott City, both of Md.

[73] Assignee: W. R. Grace & Co., New York, N.Y.

[21] Appl. No.: 874,207

[22] Filed: Feb. 1, 1978

[51] Int. Cl.² ............................................. C12D 13/02
[52] U.S. Cl. .................................... 435/119; 435/911
[58] Field of Search ........................................... 195/81

[56] References Cited

U.S. PATENT DOCUMENTS

| 3,428,526 | 2/1969 | Sigg et al. | 195/81 |
| 3,764,671 | 10/1973 | Closse et al. | 195/81 |

*Primary Examiner*—Alvin E. Tanenholtz
*Attorney, Agent, or Firm*—Philip M. Pippenger

[57] ABSTRACT

Process for the production of monorden through cultivation of *Diheterospora chlamydosporia*. Cultivation takes place in a nutrient medium and the monorden is isolated by adsorption or extraction.

5 Claims, No Drawings

PRODUCTION OF MONORDEN

The invention description below was conceived and/or reduced to practice with funds provided by the Department of Health, Education and Welfare under contract NO1-CM-67074.

DESCRIPTION OF THE INVENTION

The present invention relates to a new process for the production of monorden. This compound is also known as radicicol and using either of the above names has been described by R. N. Mirrington, E. Ritchie, C. W. Shoppee, W. C. Taylor, Tetrahedron Letters No. 7, page 365, 1963 and F. McCapra, A. I. Scott, Tetrahedron Letters No. 15, page 869, 1964. The production of monorden using novel species of the fungus *Humicola gresea* Traaen (Fungi imperfecti, Moniliales) has also been described in U.S. Pat. No. 3,428,526.

The present invention provides a process for the production of monorden characterized in that *Diheterospora chlamydosporia* is cultivated in conventional nutrient medium and monorden is isolated from said culture medium using conventional means, e.g. by adsorption or extraction. A culture of *Diheterospora chlamydosporia* employed in the present invention has been deposited with the United States Department of Agriculture (Northern Utilization Research and Development Division), Peoria, Ill. under reference no. NRRL 11178. The *Diheterospora chlamydosporia* organism is a commonly available mold having a floccose hyphal morphology characterized as follows:

Aleurospores: Spore stage, conspicuous, large (10–25 microns in diameter), muriform and sub-globose in outline. This spore initiates as a vesicle with no cross-walls; as it matures, walls at right angles are produced, and finally, a large criss-cross walled spore is formed.

Phialospores: Small, 1.5–2.5μ, sub-globose to elliptical in outline. Hyaline in microscopic preparations.

Hyphae: 1 to 2μ in width, hyaline, and appear white in colony mass.

Culture characteristics: White and floccose, approximately 4 cm. in diameter on potato dextrose agar or on Czapek's synthetic agar after eight days.

For the process of the present invention it is possible to use mutants of *Diheterospora chlamydosporia* obtained by ultraviolet or X-ray radiation or by chemical means, e.g. treatment of laboratory cultures with suitable chemicals. *D. chlamydosporia* is cultured on various nutrient media containing conventional nutrients. For example, nutrients suitable for carbon-heterotrophic organisms can be employed; specific examples of the carbon source are glucose, starch, dextrin, lactose and cane sugar; as the nitrogen source organic or inorganic nitrogen containing compounds may be used, specific examples being peptone, yeast and meat extracts (e.g. potato dextrose agar or trypticase soy agar), ammonium sulphate, ammonium nitrate and amino acids; the usual mineral salts and trace elements are also suitable for use in the nutrient.

One method of producing monorden comprises inoculating a liquid nutrient medium with a culture of *D. chlamydosporia* (cultured on potato dextrose agar or trypticase soy agar). The nutrient medium is cultured at a temperature of from about 20° to about 35° C. for a period of from about 2 to about 15 days. If the culture period is less than about 2 days, the yields of monorden are too small to be practical and if the culture period exceeds about 15 days, the process becomes unattractive in view of the amount of time and energy expended in the culture process. Preferably, the temperature employed is from about 24° to about 30° C.

The cultivation may be carried out using a static surface culture or in a submerged culture while shaking or in fermenters while aerating with air or oxygen. Following the culture period, the broth is filtered and the monorden is isolated by extractive or adsorptive methods conventionally employed. One method especially suitable for isolating monorden is solvent extraction from the fermentation broth using methylene chloride as solvent. However, other solvents may be employed such as benzene, butyl acetate, methyl acetate, chloroform or butanol. Subsequently, the extracts are separated from the solvent, e.g. by evaporation or distillation, and the residue is purified chromatographically by adsorbing agents, e.g. activated alumina, silica gel or magnesium silicate, or by means of counter current distribution. Using the above procedure monorden is isolated having physical characteristics recorded in the literature, e.g. mp 195°, ultraviolet spectrum maximum at 265 mμ; infrared spectrum bands at 3100, 2980, 1655, 1572, 1430, 1352, 1310, 1245, 1110, 1045, 983, 925, 845 $cm^{-1}$ (KBr) and nuclear magnetic resonance spectra inter alia δ1.52 (doublet) and at δ6.68 (singlet) with a molecular formula of $C_{18}H_{17}O_6Cl$.

EXAMPLE 1

*Diheterospora chlamydosporia* was maintained on potato dextrose agar and a spore suspension (approximately 1 ml.—$10^6$ to $10^8$ spores per 100 ml.) was prepared by addition of sterile distilled water to the agar slant. The suspension was used as inoculum for 100 ml. of medium contained in a 250 ml. Erlenmeyer flask. The medium had the following composition:

|  | Wt. % |
| --- | --- |
| glucose | 4 |
| cottonseed meal | 0.3 |
| corn germ meal | 0.1 |
| soybean oil meal | 0.1 |
| $K_2HPO_4$ | 0.1 |
| $MgSO_4 . 7H_2O$ | 0.1 |
| $FeSO_4 . 7H_2O$ | 0.001 |
| $CaCO_3$ | 1 |
| NaCl | 0.5 | and demineralized water to make up 100 ml. The water contained about 1 drop of an antifoaming agent (Hodag FD-62 Antifoam—10% aqueous emulsion of methyl polysiloxane).

Numerous other flasks were prepared in a similar manner and incubated on a rotating shaker at 150 rpm, 25° C. for 5 days. The contents of the flasks were combined and filtered. Eight liters of the filtered fermentation broth were extracted with methylene chloride (1:4, V/V). This extraction was carried out three times, and the methylene extracts were combined. $CH_2Cl_2$ was removed under reduced pressure to yield a syrup which was chromatographed on 8×20 cm. column of silica gel (0.063–0.2 mm) by elution chromatography using chloroform as eluent. The monorden formed white crystals with a melting point of 191.5°–192° (uncorrected) and having the UV, IR and nmr ($CDCl_3$) set forth above for monorden. The yield of monorden was approximately 45 mg./liter of the filtered fermentation broth.

The mycelium was mixed with CH$_2$Cl$_2$ in a 1:1 (V/V) ratio and stirred vigorously for 10 minutes (in a Waring blender). The solvent was separated and the process was repeated three times. The extracts were combined and the methylene chloride was removed by distillation and chromatographed as above. The yield of monorden was 60 mg./liter.

What is claimed is:

1. A process for the production of monorden which comprises cultivating *Diheterospora chlamydosporia* or a mutant thereof in a nutrient solution containing a source of carbon, nitrogen and mineral salts, and isolating monorden from said nutrient solution.

2. The process according to claim 1 wherein the nutrient solution is cultured at a temperature of from about 20° to about 35° C.

3. A process as in claim 1 wherein the nutrient solution is cultured for from about 2 to about 15 days.

4. A process as in claim 1 wherein monorden is separated from the nutrient solution by solvent extraction.

5. A process as in claim 4 and including the further step of isolating monorden from the solvent extract.

* * * * *